United States Patent [19]

Atwal et al.

[11] Patent Number: 5,453,421
[45] Date of Patent: Sep. 26, 1995

[54] ARYL AND HETEROCYCLIC SUBSTITUTED PROPENAMIDE DERIVATIVES

[75] Inventors: Karnail S. Atwal, Newtown, Pa.; Syed Z. Ahmed, Pennington; Dinos P. Santafianos, Maplewood, both of N.J.

[73] Assignee: E. R. Squibb & Sons, Inc., Princeton, N.J.

[21] Appl. No.: 103,053

[22] Filed: Aug. 12, 1993

Related U.S. Application Data

[63] Continuation-in-part of Ser. No. 944,137, Sep. 11, 1992, abandoned.

[51] Int. Cl.$^6$ .................. A61K 31/35; A61K 31/665; C07D 311/68; C07F 9/655
[52] U.S. Cl. .................. 514/100; 514/456; 549/404; 549/399; 549/345; 549/200
[58] Field of Search .................. 549/404, 399, 549/345, 220; 514/456, 100; 548/525; 546/207; 544/376, 151, 62; 540/524

[56] References Cited

U.S. PATENT DOCUMENTS

| | | |
|---|---|---|
| 3,953,506 | 4/1976 | Spicer et al. |
| 5,140,031 | 8/1992 | Atwal et al. |

FOREIGN PATENT DOCUMENTS

| | | |
|---|---|---|
| 0126311A3 | 11/1984 | European Pat. Off. |
| 205292 | 12/1986 | European Pat. Off. |
| 214818 | 3/1987 | European Pat. Off. |
| 274821 | 7/1988 | European Pat. Off. |
| 344747 | 12/1989 | European Pat. Off. |
| 350805 | 1/1990 | European Pat. Off. |
| 359537 | 3/1990 | European Pat. Off. |
| 0377966A3 | 7/1990 | European Pat. Off. |
| 389861 | 10/1990 | European Pat. Off. |
| 0407200A1 | 1/1991 | European Pat. Off. |
| 412531 | 2/1991 | European Pat. Off. |
| 462761 | 12/1991 | European Pat. Off. |
| 488616 | 6/1992 | European Pat. Off. |
| WO8707607 | 12/1987 | WIPO |
| 91/09031 | 6/1991 | WIPO |
| 92/22293 | 12/1992 | WIPO |

OTHER PUBLICATIONS

Albrecht et al., "Chemotherapeutic nitroheterocycles. XI (1). Indanylamides and indanylesters of 5-nitrofurancarboxylic acids and analogous compounds as antimicrobial agents", *Chimie Therapeutique*, vol. 7, No. 1, 1972, pp. 9–13.

H. J. Petersen et al., *J. of Med. Chem.*, vol. 21, No. 8, 1978:773–781, Washington, D.C.

V. A. Ashwood et al., "Synthesis and Antihypertensive Activity of 4-(cyclic amido)-2H-1-benzopyrans", *J. Med. Chem.*, 1986:29:2194–2201.

C. R. Rasmussen et al., "Improved Procedures of Cycloalkyl-, Arylalkyl-, and Arylthioureas", *Synthesis*, Juen 1988:456–459.

V. V. Mozolis et al., "Preparation of N-Substituted Thiourea", *Russian Chemical Reviews*, 42(7):1973:587–595.

J. M. Evans et al., "Synthesis and Antihypertensive Activity of Su,bstituted trans-4-Amino-3,4-dihydro-2,2-dimethyl-2H-1-benzopyran-3-Ols", *J. Med. Chem.*, 1983:26:1582–1589.

R. W. Lang et al., "Synthesis of Selectivity Tribluoromethylated Pyridine Derivatives as Potential Antihypertensives", *Helvetica Chimica Acta*, 1988:71:596–601.

P. Sebok et al., "Selective Synthesis of Analogues of the Natural Prococenes Synthesis and Regioselective (−Alkylation of 6-Chloro- and 6-Tert-Butyl-7, 8-Dihydroxy-2,2-Dimethyl-4-Chromanones", *Heterocycles*, 1988:27:2595–2607.

P. Teixidor et al., "Improved Preparation of Precocene II, Unexpected Results in the Reduction of Alkoxy Substituted Acetophenones and 4-Chromanones with Sodium Borohydride", *Heterocycles*, 1988:27:2459–2465.

A. Banerji et al., "Enolats of o-Hydroxyacetophenones: Novel Synthesis of 2,2-Dialkyl-4-Chromanones", *Tetrahedron Let.*, 1979:38:3685–3686.

G. Ariamala et al., "A Simple Route for the Synthesis of 4-Chlorochromenes and Chroman-4-ones", Tetrahedron Let., 1988:vol. 29, No. 28:3487–3488.

R. Albrecht et al., CA77:88182j (1972), Abstract of Chim. Ther., 1972:7(1):90–13.

*Primary Examiner*—Nicky Chan
*Attorney, Agent, or Firm*—Ellen K. Park

[57] ABSTRACT

Novel compounds useful, for example, for the treatment of ischemic conditions and arrhythmia are disclosed. The compounds have the formula

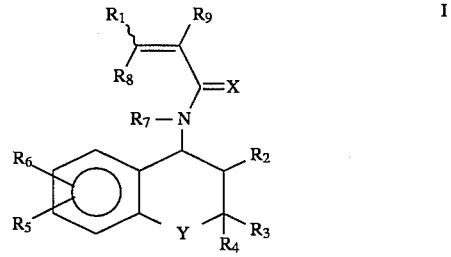

wherein X is oxygen or sulfur and the R groups are as defined herein.

10 Claims, No Drawings

ARYL AND HETEROCYCLIC SUBSTITUTED PROPENAMIDE DERIVATIVES

This application is a continuation-in-part of U.S. application Ser. No. 07/944,137, filed Sep. 11, 1992, now abandoned.

SUMMARY OF THE INVENTION

In accordance with the present invention novel compounds having potassium channel activating activity and useful for example, as antiischemic agents are disclosed. These compounds have the general formula

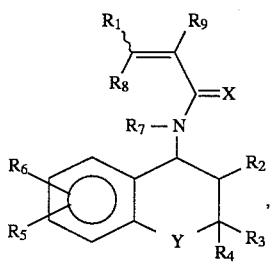

I and pharmaceutically acceptable salts thereof, wherein

X is oxygen or sulfur;

$R_1$ is aryl or heterocyclo;

$R_2$ is hydrogen, hydroxy or

$R_3$ and $R_4$ are each independently hydrogen, alkyl or arylalkyl; or, $R_3$ and $R_4$ taken together with the carbon atom to which they are attached form a 5- to 7-membered carbocyclic ring;

$R_5$ is hydrogen, alkyl, haloalkyl, alkenyl, alkynyl, cycloalkyl, arylalkyl, cycloalkylalkyl, —CN, —NO$_2$, —COR, —COOR, —CONHR, —CON(R)$_2$, —CF$_3$, —S-alkyl, —SOalkyl, —SO$_2$alkyl

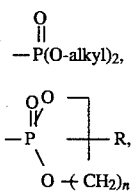

halogen, amino, substituted amino, —O-alkyl, —OCF$_3$, —OCH$_2$CF$_3$, —OCOalkyl, —OCONRalkyl, —NRCOalkyl, —NRCOOalkyl or —NRCON(R) wherein R is hydrogen, alkyl, aryl, arylalkyl, cycloalkyl, or (cycloalkyl)alkyl or haloalkyl;

$R_6$ is hydrogen, alkyl, halo, —OH, —O-alkyl, amino, substituted amino, —O-alkyl, —OCOalkyl, —OCONRalkyl, —NR COalkyl, —NRCOOalkyl or —NRCON(R)$_2$;

$R_7$ is hydrogen, alkyl or arylalkyl;

$R_8$ is hydrogen, alkyl, aryl or —O-alkyl;

$R_9$ is hydrogen, alkyl, aryl, —COO-alkyl or —CO-alkyl; or $R_1$ and $R_8$ or $R_1$ and $R_9$ or $R_8$ and $R_9$ and the atoms to which they are attached complete a 5- to 7- membered carbocyclic or heterocyclic ring; or $R_7$ and $R_8$ and the atoms to which they are attached complete a 5- to 7-membered ting which may contain 1 or 2 hetero atoms;

Y is a single bond, —O—, —S— or —CR$_{10}$R$_{11}$ wherein $R_{10}$ and $R_{11}$ are independently hydrogen or alkyl, with the proviso that if one or both of $R_{10}$ and $R_{11}$ are alkyl, then $R_3$ and $R_4$ are each hydrogen and if one or both of $R_3$ and $R_4$ are alkyl, then $R_{10}$ and $R_{11}$ are each hydrogen; and n is an integer of 1, 2 or 3.

DETAILED DESCRIPTION OF THE PRESENT INVENTION

Throughout the present application, the following definitions apply to the terms used herein.

The term "alkyl" used in defining various symbols refers to straight or branched chain saturated hydrocarbon radicals having up to eight carbons, preferably from one to five carbons. Similarly, the terms "alkoxy" and "alkylthio" refer to such alkyl groups attached to an oxygen or sulfur.

The term "alkenyl" refers to straight or branched chain hydrocarbon radicals having from two to eight carbons and at least one double bond, preferably three to five carbons.

The term "alkynyl" refers to straight or branched chain hydrocarbon radicals having from two to eight carbons and at least one triple bond, preferably three to five carbons.

The term "cycloalkyl" refers to saturated carbocyclic rings of three to seven carbon atoms with cyclopropyl, cyclopentyl and cyclohexyl being most preferred.

The term "halo" or "halogen" refers to chlorine, bromine, iodine or fluorine.

The term "halo substituted alkyl" or "haloalkyl" refers to such alkyl groups described above in which one or more hydrogens have been replaced by a halogen such as chloromethyl, bromomethyl, trifluoromethyl, pentafluoroethyl, 2,2,2-trichloroethyl or 2,2,2-trifluoroethyl. Trifluoromethyl is preferred.

The term "aryl" refers to phenyl, 1-naphthyl, 2-naphthyl or mono substituted phenyl, 1-naphthyl, 2-naphthyl wherein said substituent is alkyl of 1 to 4 carbons, (amino)alkyl, (substituted amino)alkyl, alkylthio of 1 to 4 carbons, alkoxy of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons, haloalkyl, —O(haloalkyl),

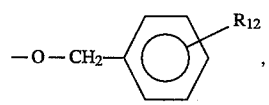

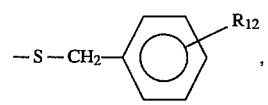

(wherein $R_{12}$ is hydrogen, alkyl of 1 to 4 carbons, alkoxy of 1 to 4 carbons, alkylthio of 1 to 4 carbons, halo, hydroxy or —CF$_3$), —O—CH$_2$-cycloalkyl, —S—CH$_2$-cycloalkyl, or —alkyl(COOR$_{13}$) (where $R_{13}$ is hydrogen or alkyl), and disubstituted phenyl, 1-naphthyl, 2-naphthyl wherein said substituents are selected from methyl, methoxy, methylthio, halo, —CF$_3$, nitro, amino, —OCHF$_2$ or —alkyl(COOR$_{13}$).

Preferred aryl groups include unsubstituted phenyl and monosubstituted phenyl wherein the substituents are nitro, halo, —CF$_3$, alkyl, cyano, methoxy or —alkyl(COOR$_{13}$).

The term "heterocyclo" refers to fully saturated or unsaturated rings of 5 or 6 atoms containing one or two O and S atoms and/or one to four N atoms provided that the total number of hetero atoms in the ring is 4 or less. The hetero ring is attached by way of an available atom. Preferred monocyclic heterocyclic groups include 2- and 3-thienyl, 2- and 3-furyl, 2-, 3- and 4-pyridyl, and imidazolyl. The term heterocyclo also includes bicyclic rings wherein the five or six membered ring containing O, S and N atoms as defined above is fused to a benzene ring and the bicyclic ring is attached by way of an available carbon atom. Preferred bicyclic hetero groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxaiazolyl, and 4, 5, 6 or 7-benzofuranzanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —NH-alkyl wherein alkyl is of 1 to 4 carbons, —N(alkyl)$_2$ wherein alkyl is of 1 to 4 carbons, —CF$_3$, or —OCHF$_2$ or such monocyclic and bicyclic rings wherein two or three available carbons have substituents selected from methyl, methoxy, methylthio, halo, —CF$_3$, nitro, hydroxy, amino and —OCHF$_2$.

The term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkylalkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

The compounds of formula I, wherein X is oxygen, can be prepared by reacting a compound of the formula

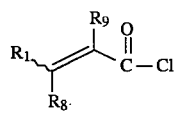

II with an amine of the formula

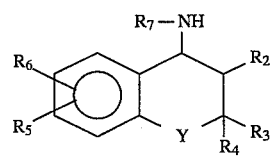

III in an organic solvent, such as dimethylformamide, tetrahydrofuran, acetonitrile or dichloromethane. A suitable starting material of formula II is cinnamyl chloride. Other compounds of formula II are commercially available or may be prepared according to literature methods.

Alternatively, the compounds of formula I where X is oxygen can be prepared by reacting an acid of the formula

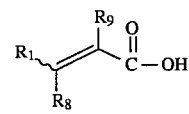

IV with an amine of formula III in the presence of a carbodiimide such as dicyclohexyl-carbodiimide or 1-(3-dimethylaminopropyl)-2-ethylcarbodiimide hydrochloride.

Compounds of formula I wherein X is sulfur, can be prepared by treatment of a compound of formula I wherein X is oxygen with P$_4$S$_{10}$ or Lawesson's reagent.

The aminoalcohol of formula III wherein R$_2$ is trans hydroxy and Y is oxygen can be prepared by methods described in the literature, such as by J. M. Evans, C. S. Fake, T. C. Hamilton, R. H. Poyser, E. A. Watts, *J. Med. Chem.*, 1983, 26, 1582 and *J. Med. Chem.*, 1986, 29, 2194; R. W. Lang, P. F. Wenk, *Helvetica Chimica Acta*, 1988, 71, 596; EP 0205292 A2 (1986), and WO 87/07607. The aminoalcohol of formula III when R$_2$ is cis hydroxy and Y is oxygen can be prepared by methods described by G. Burrell, J. M. Evans, G. E. Jones and G. Stemp, *Tetrahedron Letters*, Vol. 31, p. 3649 (1990).

Amines of formula III wherein Y is a single bond can be prepared according to D. R. Buckle et al., *Journal of Medicinal Chemistry*, 1991, V. 34, p. 919. Amines of formula III wherein Y is methylene can be prepared by methods described in V. A. Ashwood et al. (*J, Med. Chem.*, 1991, V. 34, 3261).

The amine of formula III, wherein R$_2$ is hydrogen, can be prepared from a ketone of the formula

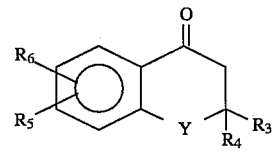

V by standard methodology. The ketone of formula V can be obtained by literature procedures, such as disclosed by P. Sebok and T. Timar, *Heterocycles*, 1988, 27, 2595; P. Teixidor et al., *Heterocycles*, 1988, 27, 2459; A. Benerji and N. C. Goomer, *Tetrahedron Letters*, 1979, 3685; G. Ariamala and K. K. Subramanian, *Tetrahedron Letters*, Vol. 29, No. 28, p. 3487–3488 (1988).

The amine of formula III wherein R$_2$ is hydrogen, can also be prepared from the olefin of formula

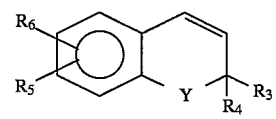

VI by a sequence of steps which involve: (a) catalytic hydrogenation of the double bond, (b) bromination of the resulting compound with N-bromosuccinimide and light, (c) displacement of the bromide with azide using sodium azide followed by (d) catalytic reduction of the azide.

The olefin of formula VI can be prepared from the ketone of formula V by reduction (using for example, sodium borohydride) and dehydration (using for example, p-toluenesulfonic acid and heat).

For the preparation of individual enantiomers of compounds of formula I the enantiomers of amine III can be prepared and reacted as described above. To prepare enantiomers of amine III wherein $R_2$ is transhydroxyl, the olefin of formula VI is epoxidized with commercial bleach using a chiral manganese catalyst

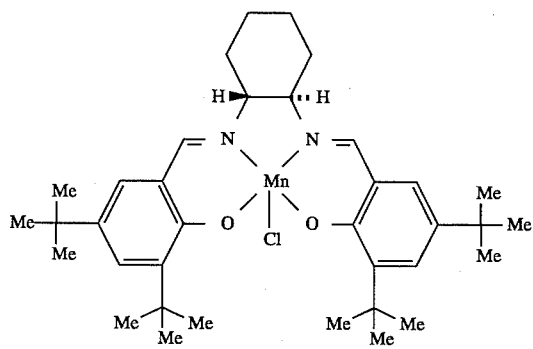

VII as described by N. H. Lee et at. (*Tetrahedron Letters*, 1991, V. 32, p. 5055–5058), to provide predominantly the chiral epoxide of formula

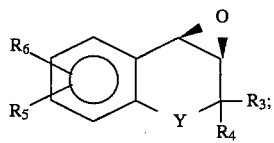

VIII and

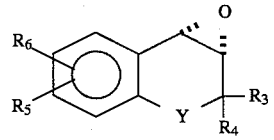

IX depending on the chirality of 1,2-diaminocyclohexane used in the preparation of VII.

The epoxides of formula VIII and IX can be reacted with an amine of formula $R_7NH_2$ to provide enantiomers of amine III wherein $R_2$ is trans-hydroxyl.

For the preparation of enantiomers of other compounds of formula I, the amine of formula III is convened to diastereomeric amides of formula

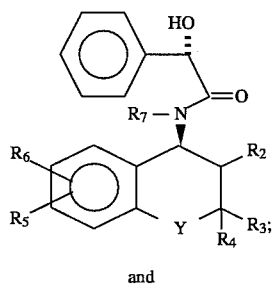

X and

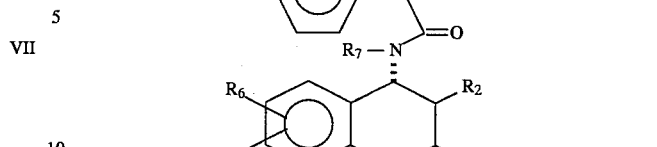

XI by treatment with chiral nonracemic mandelic acid in the presence of dicyclohexylcarbodiimide.

Compounds of formula X and XI may be separated by crystallization or chromatography.

The enantiomer of mandelic acid that yields the crystalline amide with the desired stereochemistry is preferred in the resolution step.

Compounds X and XI are then hydrolyzed by heating in dioxane in the presence of sulfuric acid to give enantiomers of formula

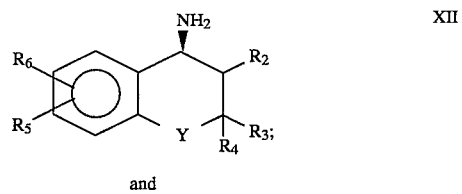

XII and

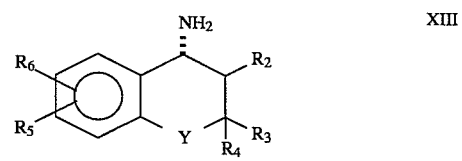

XIII

The compounds of the present invention can have asymmetric centers at carbon atoms of the bicyclic ring. Also, any one of the R groups can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

Preferred compounds of formula I are those wherein $R_1$ is aryl or heterocyclo;

$R_2$ is hydrogen or hydroxy;

$R_3$ and $R_4$ are each alkyl;

$R_5$ is an electron withdrawing group, such as —CN, —$NO_2$, —COR, —COOR, —CONHR, —CON(R)$_2$, —$CF_3$, —SOalkyl, —$SO_2$alkyl,

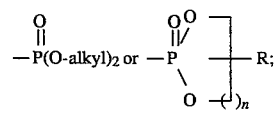

$R_6$ is hydrogen, alkyl or O-alkyl;

$R_7$ is hydrogen;

$R_8$ is hydrogen;

$R_9$ is hydrogen; or $R_1$ and $R_9$ and the atoms to which they are attached complete a 5- to 7- membered carbocyclic or heterocyclic ring.

Most preferred are those compounds wherein $R_1$ is phenyl, 4-chlorophenyl or 4-fluorophenyl;

$R_2$ is trans-hydroxy;

$R_3$ and $R_4$ are each methyl;

$R_5$ is —CN or —$NO_2$;

$R_6$ is hydrogen;

$R_7$ is hydrogen;

$R_8$ is hydrogen;

$R_9$ is hydrogen;

where $R_1$ and $R_9$ are in a trans arrangement; or $R_1$ and $R_9$ and the atoms to which they are attached complete an oxazole, thiadiazole, triazole, cyclopentane or aryl ring.

The compounds of formula I and the pharmaceutically acceptable salts thereof act as potassium channel activators. More particularly the compounds of formula I and the pharmaceutically acceptable salts thereof are useful as anti-ischemic agents since they have been found to possess little or no antihypertensive activity. The selectivity means that in the treatment of, for example, ischemic heart disease, these compounds are less likely to cause coronary steal, profound hypotension and coronary underperfusion. By little or no vasodilation activity is meant that these compounds have $IC_{50}$ (rat aorta) values greater than that of the potassium channel activator, cromakalim. The "selective" antiischemic agents typically are those having $IC_{50}$ (rat aorta) values >10 times that of cromakalim (i.e., have 1/10 the vasodilatory action) and preferably those having $IC_{50}$ values >50 times that of cromakalim. Thus, compounds of formula I are useful for the treatment of ischemic conditions, e.g. myocardial ischemia, cerebral ischemia, lower limb ischemia, i.e., peripheral vascular disease, and the like.

Thus, for example, by the administration of a composition containing one (or a combination) of the compounds of this invention, ischemic conditions of a mammalian (e.g., human) host are reduced. A single dose, or preferably two to four divided daily doses, provided on a basis of about 0.001 to 100 mg per kilogram of body weight per day, preferably from about 0.1 to about 25 mg per kilogram per day, is appropriate to reduce ischemic conditions. The substance is preferably administered orally, but parenteral routes, such as the subcutaneous, intramuscular, or intravenous routes or any other convenient delivery system, such as inhalation or intranasal solutions or transdermal patches, can also be employed. The above doses are also suitable for the other cardiovascular and non-cardiovascular uses.

As a result of the potassium channel activating activity of compounds of this invention, these compounds are also useful in the treatment of other cardiovascular disorders. For example, compounds of the present invention are useful as therapy for congestive heart failure, as anti-anginal agents, as anti-fibrillatory agents, as antiarrhythmic agents and in limiting myocardial infarction.

Compounds of the present invention are additionally expected to be useful in the treatment of central nervous system disorders (e.g., Parkinsonism, as anti-tremor agents, epilepsy).

The compounds of this invention can also be formulated in combination with a diuretic such as, chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to 500 milligrams of a compound of formula I is compounded with physiologically acceptable vehicle, carder, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the preferred embodiments of the invention and are illustrative rather than limiting. It should be understood that there may be other embodiments which fall within the spirit and scope of the invention as defined by the claims appended hereto.

EXAMPLE 1

[3S-[3α,4β(E)]]-N-(6-Cyano-3,4-dihydro-3-hydroxy-2,2-dimethyl-2H-1-benzopyran-4-yl)-3-phenyl-2-propenamide A. (1aR-cis-1a,7b-Dihydro-2,2-dimethyl-2H-oxireno-[c][1]-benzopyran-6-carbonitrile A solution of 0.05M $Na_2HPO_4$ (10 mL) was added to a solution of undiluted commercial house hold bleach (25 mL). Sodium hydroxide (1N solution) was added dropwise to the resulting solution (0.55M in NaOCl) until pH ~11.3. This solution was cooled to 0° C. and then added to cold (0° C.) solution of Mn (III) salen complex (0.26 g, 0.4 retool, described by N. H. Lee et al., *Tetrahedron Letters*, 1991, V. 32, p. 5055) and 6-cyano- 2,2-dimethyl-2H-1-benzopyran (1.85 g, 10 mmol, prepared according to Evansetal., *J. Med. Chem.*, 1986, 29, p. 2194and *J. Med. Chem.*, 1983, 26, p. 1582) in dichloromethane (10 mL). The two phase reaction mixture was stirred at 0° C. and monitored by TLC. After eight hours, the heterogenous brown mixture was filtered through a pad of celite and the organic phase was separated. It was washed with brine (50 mL), dried over anhydrous magnesium sulfate and concentrated in vacuo to yield a light yellow solid (2.0 g, 99%). The solid was recrystallized from aqueous ethanol to give the title A compound as a white solid (0.6 g), m.p. 128°–133° C. $^1$HNMR ($CDCl_3$) δ7.58 (d, J=2.3 Hz, 1H), 7.46 (dd, J=2.3 & 1.7 Hz 1H), 6.79 (d, J=8.2 Hz, 1H), 3.84 (d, J=4.1 Hz, 1H), 3.47 (d, J= 4.1 Hz, 1H), 1.53

(s, 3H), 1.22 (s, 3H). $^{13}$CNMR(CDCl$_3$) δ156.4, 134.4, 133.8, 121.1, 119.0, 118.7, 104.2, 74.6, 62.2, 49.8, 25.4, 22.9. $[\alpha_D]^{25}$=+80.7° (c=1.166, MeOH).

Analysis calculated for C$_{12}$H$_{11}$NO$_2$.0.09H$_2$O: C, 71.05; H, 5.56; N, 6.91; Found: C, 71.18; H, 5.39; N, 6.78.

B. (3S-trans)-4-Amino-3,4-dihydro-3-hydroxy-2, 2-dimethyl-2H-1-benzopyran-6-carbonitrile To a solution of the title A compound (3.0 g, 15.0 mmol) in ethanol (30 mL) and tetrahydrofuran (30 mL) was added ammonium hydroxide (30 mL) and the reaction mixture was heated at 50° C. in a pressure bottle for 16 hours. Most of the solvent was evaporated and the residue was dissolved in 1N hydrochloric acid. It was extracted with ether and the organic extracts were discarded. The aqueous layer was made basic by the addition of 1N sodium hydroxide and extracted with chloroform. The combined organic extracts were washed with brine and dried over anhydrous magnesium sulfate. The solvent was evaporated to yield the title B compound (2.8 g, 86%), as a colorless foam. This material was used for the next reaction without further purification.

C. [3S-[3α,4β(E)]]-N-(6-Cyano-3,4-dihydro-3-hydroxy-2,2-dimethyl-2H-1-benzopyran-4-yl)-3-phenyl-2-propenamide To a solution of the title B compound (1.0 g, 4.6 mmol) in 20% aqueous THF (20 mL) was added a solution of cinnamyl chloride (0.86 g, 5.1 mmol) in THF (10 mL) while maintaining the pH of the reaction mixture between 8.5–9.0 by simultaneous addition of 25% aqueous sodium carbonate at room temperature. After completion of addition, the reaction was stirred for one hour and then concentrated in vacuo. The residue was diluted with ethyl acetate (250 mL) and washed with water. After drying over anhydrous magnesium sulfate, the solvent was evaporated and the residue was purified by trituration with ethyl ether to yield [3S-[3α, 4β(E)]]-N-(6-cyano-3,4-dihydro-3-hydroxy-2,2-dimethyl-2H-1-benzopyran-4-yl)-3-phenyl-2-propenamide (1.0 g, 62.6 %), m.p. 117°–120° C.: $^1$H NMR (DMSO-d$_6$) δ8.61 (d, J=8.8 Hz, 1H), 7.60 (m, 4H), 7.45 (t, J=8.8 & 15.9 Hz, 4H), 6.95 (d, J=8.8 Hz, 1H), 6.70 (d, J= 15.8 Hz, 1H), 5.77 (d, J=5.9 Hz, 1H), 4.95 (t, J=8.8 & 17.6 Hz, 1H), 3.64 (dd, J=5.9 & 15.8 Hz, 1H), 1.44, 1.21 (s, 3H each); $^{13}$C NMR (DMSO-d$_6$) 166.7, 156.9, 140.0, 135.4, 133.4, 133.3, 130.2, 129.6, 128.2, 125.6, 122.6, 119.6, 118.6, 103.4, 80.9, 71.8, 49.4, 27.1, 19.5; IR (KBr) 1267.1, 1491.2, 1532.2, 1615.2, 1657.2, 2226.1, 3418.2 cm$^{-1}$, $[\alpha_D]^{25}$= –36.3° (c=0.9167, MeOH).

Analysis calculated for C$_{21}$H$_{20}$N$_2$O$_3$.0.13 H$_2$O: C, 71.90; H, 5.82; N, 7.99; Found: C, 71.80; H, 5.63; N, 8.09.

EXAMPLE 2

[3S-[3α,4β(E)]]-3-(4-Chlorophenyl)-N-(6-cyano-3, 4-dihydro-3-hydroxy-2.2-dimethyl-2H-1-benzopyran-4-yl)-3-phenyl-2-propenamide To a solution of the title B compound of Example 1 (3S-trans)-4-amino-3,4-dihydro-3-hydroxy-2,2-dimethyl-2H-1-benzopyran-6-carbonitrile (1.0 g, 4.6 mmol) in dimethylformamide (3 mL) was added 4-chlorocinnamic acid (0.84 g, 4.6 mmol), followed by 1-(3-dimethylaminopropyl)-2-ethyl-carbodiimide hydrochloride (1.3 g, 6.9 mmol). The reaction mixture was stirred for two hours and then poured into water (50 mL). It was extracted with ethyl acetate (250 mL) and the combined extracts were washed with water (3×100 mL). After drying over anhydrous magnesium sulfate, the solvent was evaporated and the residue was purified by flash chromatography eluting with hexane/ ethyl acetate (1:1) to yield a colorless solid (1.3 g). The solid was triturated with hexane to give [[3S-[3α,4β(E)]]-3-(4-chlorophenyl)-N-(6-cyano-3,4-dihydro-3-hydroxy-2,2-dimethyl-2H-1-benzopyran-4-yl)-3-phenyl-2-propenamide (1.1 g), m.p. 125°–128° C.: $^1$H NMR (CDCl$_3$) δ7.65 (d, J= 11.7 Hz, 2H), 7.45 (d, J=8.2 Hz, 3H), 7.35 (d, J=8.8 Hz, 2H), 6.90 (d, J=8.8 Hz, 1H), 6.75 (d, J=8.3 Hz, 1H), 6.70 (d, J=15.8 Hz, 1H), 5.26 (t, J=8.8 & 17.0 Hz, 1H), 4.34 (br s 1H), 3.82 (d, J=9.4 Hz, 1H), 1.60, 1.35 (s, 3H each); $^{13}$C NMR (CDCl$_3$) 169.0, 157.6, 142.0, 136.6, 133.7, 133.1, 132.9, 129.6, 122.9, 120.1, 119.1, 104.1, 80.8, 76.1, 51.2, 26.8, 18.9; IR (KBr) 1267.4, 1491.7, 1532.2, 1615.2, 1661.4, 2226.2, 3331.2 cm$^{-1}$, $[\alpha_D]^{25}$ =–28.9° (c=0.817, MeOH).

Analysis calculated for C$_{21}$H$_{19}$ClN$_2$O$_3$.0.15H$_2$O: C, 65.41; H, 5.05; N, 7.27; Cl, 9.19; Found: C, 65.65; H, 4.92; N, 7.03; Cl, 9.50.

EXAMPLE 3

[3S-[3α,4β(E)]]-3-(3-Chlorophenyl)-N-(6-cyano-3, 4-dihydro-3-hydroxy-2.2-dimethyl-2H-1-benzopyran-4-yl)-2-propenamide To a solution of the title B compound of Example 1 (3S-trans)-4-amino-3,4-dihydro-3-hydroxy-2,2-dimethyl-2H-1-benzopyran-6-carbonitrile (1.0 g, 4.6 mmol) in dimethylformamide (3 mL) was added 3-chlorocinnamic acid (0.84 g, 4.6 mmol), followed by 1-(3-dimethylaminopropyl)- 2-ethyl-carbodiimide hydrochloride (1.3 g, 6.9 mmol). The reaction mixture was stirred for two hours and then poured into water (50 mL). It was extracted with ethyl acetate (250 mL) and the combined extracts were washed with water (3×100 mL). After drying over anhydrous magnesium sulfate, the solvent was evaporated and the residue was purified by flash chromatography, eluting with hexane/ ethyl acetate (1:1). The product (1.2 g) was triturated with hexanes to give [[3S-[ 3α,4β(E)]]-3-(3-chlorophenyl)-N-(6-cyano-3,4-dihydro-3-hydroxy-2,2-dimethyl-2H-1-benzopyran-4-yl)-3-phenyl-2-propenamide (0.9 g), as a colorless solid, m.p. 206°–208° C. $^1$H NMR (CDCl$_3$/DMSO-d$_6$) δ7.75 (d, J= 11.7 Hz, 1H), 7.32 (m, 6H), 6.60 (d, J=8.8 Hz, 1H), 6.43 (d, J=15.9 Hz, 1H), 4.85 (t, J=8.8 & 17.0 Hz, 1H), 3.70 (s, 2H), 3.45 (d, J=10.0 Hz, 1H), 1.24, 1.03 (s, 3H each); $^{13}$C NMR (CDCl$_3$/DMSO-d$_6$) 165.4, 155.3, 137.2, 135.7, 133.1, 131.6, 131.1, 129.0, 127.9, 125.9, 124.7, 123.3, 121.9, 117.7, 116.7, 101.9, 79.0, 70.9, 48.2, 25.3, 17.6; IR (KBr) 1267.2, 1489.3, 1613.2, 1667.2, 2228.1, 3333.2 cm$^{-1}$. $[\alpha_D]^{25}$=–35.4° (c=0.817, MeOH).

Analysis calculated for C$_{21}$H$_{19}$ClN$_2$O$_3$.0.36H$_2$O: C, 64.78; H, 5.11; N, 7.20; Cl, 9.11; Found: C, 64.70; H, 5.05; N, 7.28; Cl, 9.08.

EXAMPLE 4

[3S-[3α,4β(Z)]]-N-(6-cyano-3,4-dihydro-3-hydroxy-2,2-dimethyl-2H-1-benzopyran-4-yl)-3-phenyl-2-propenamide A. (z)-3-Phenylpropenoic acid, methylester A solution of bis-(2,2,2-trifluoromethyl)-(methoxycarbonylmethyl)phosphonate (3.2 g, 10.0 mmol) and 18-crown-6 (1.3 g, 5.0 mmol) in dry tetrahydro-furan (50 mL) was cooled to –78° under argon and treated with potassium bis(trimethylsilyl)amide (0.5M) (20 mL, 10.0 mmol). Benzaldehyde (1.1 g, 10.0 mmol) was then added and the resulting reaction mixture was stirred at −78° for one hour. The reaction mixture was quenched with saturated ammonium chloride (10 mL) and extracted with ethyl ether (3×100 mL). The combined extracts were washed with water (100 mL), dried over anhydrous magnesium sulfate and concentrated in vacuo to yield the title A compound (1.6 g). $^1$H NMR (CDCl$_3$) δ7.18 (m, 5H), 6.80 (d, J=12.3 Hz, 1H), 5.80 (d, J=12.9 Hz, 1H), 3.56 (s, 3H).

B. (z)-3-phenylpropenoic acid

A solution of (z)-3-phenylpropenoic acid, methyl ester (0.8 g, 4.9 mmol) in 20% aqueous tetrahydrofuran (5 mL) was treated with lithium hydroxide hydrate (0.42 g, 9.9 mmol) and the reaction mixture was stirred under argon at room temperature for 20 hours. It was concentrated in vacuo, diluted with water (50 mL) and extracted with dichloromethane (2×50 mL). The organic extracts were discarded and the aqueous layer was acidified to pH~3 with 1N hydrochloric acid and extracted with dichloromethane (3×100 mL). The combined extracts were dried over anhydrous magnesium sulfate and concentrated in vacuo to yield the title B compound (0.5 g). $^1$H NMR (CDCl$_3$) δ11.57 (brs, 1H), 7.48 (m, 2H), 7.25 (m, 2H), 6.94 (d, J=12.2 Hz, 1H), 5.84 (d, J=12.3 Hz, 1H).

C. [3S-[3α,4β(Z)]]-N-(6-cyano-3,4-dihydro-3-hydroxy-2,2-dimethyl-
2H-1-benzopyran-4-yl)-3-phenyl-2-propenamide To a solution of the title B compound of Example 1, (3S-trans)-4 -amino-3,4-dihydro-3-hydroxy-2,2-dimethyl-2H-1-benzopyran-6-carbonitrile (0.73 g, 3.4 mmol) in dimethylformamide (3 mL) was added (z)-3-phenylpropenoic acid (0.50 g, 3.4 mmol), followed by 1-(3 -dimethylaminopropyl)-2-ethylcarbodi-imide hydrochloride (0.83 g, 4.4 mmol). The reaction was stirred for two hours and then poured into water (50 mL). It was extracted with ethyl acetate (250 mL) and combined extracts were washed with water (3×100 mL), and dried over anhydrous magnesium sulfate. The solvent was evaporated and the residue was purified by flash chromatography eluting with hexane/ethyl acetate (1:1) to yield [3S-[3α,4β(Z)]]-N-(6-cyano-3,4-dihydro-3-hydroxy- 2,2-dimethyl-2H-1-benzopyran-4-yl)-3-phenyl-2-propenamide (0.7 g) as a colorless solid, m.p. 175°–176° C.: $^1$H NMR (DMSO-d$_6$) δ8.57 (d, J=8.8 Hz, 1H), 7.70 (d, J=6.7 Hz, 2H), 7.60 (dd, J=1.8 & 2.4 Hz, 1H), 7.35 (m, 4H), 6.92(d, J=8.8 Hz, 1H), 6.74 (d, J=12.9 Hz, 1H), 6.13 (d, J= 12.3 Hz, 1H), 5.73 (t, J=7.0 & 12.9 Hz, 1H), 4.89 (t, J=9.4&18.9 Hz, 1H), 3.60 (dd, J=3.5 Hz, 1H), 1.78 (s, 1H), 1.41, 1.19 (s, 3H each); $^{13}$C NMR (DMSO-d$_6$) 167.1, 155.3, 136.1, 135.3, 132.6, 129.6, 128.4, 128.0, 125.1, 124.4, 117.9, 102.7, 80.3, 71.1, 48.5, 26.4, 18.8; IR (KBr) 696.2, 945.2, 1069.3, 1125.3, 1267.6, 1489.7, 1522.7, 1624.5, 1651.5, 2228.3, 3401.2 cm$^{-1}$; [a$_D$]$^{25}$=−68.7° (c=0.766, MeOH).

Analysis calculated for C$_{21}$H$_{20}$N$_2$O$_3$.0.24H$_2$O: C, 71.51; H, 5.85; N, 7.94; Found: C, 71.65; H, 5.55; N, 7.80.

EXAMPLE 5

[3S-[3α,4β(E)]]-3-(4-fluorophenyl)-N-(6-cyano-3,
4-dihydro-3-hydroxy-
2,2-dimethyl-2H-1-benzopyran-4-yl)-2-propenamide To a solution of the title B compound of Example 1, (3S-trans)-4 -amino-3,4-dihydro-3-hydroxy-2,2-dimethyl-2H-1-benzopyran-6-carbonitrile 1 (0.73 g, 3.4 mmol) in dimethylformamide (3 mL) was added 3-fluorocinnamic acid (0.56 g, 3.4 mmol), followed by 1-(3-dimethylaminopropyl)- 2-ethyl-carbodiimide hydrochloride (0.83 g, 4.4 mmol). The reaction mixture was stirred for two hours and poured into water (50 mL). It was extracted with ethyl acetate (250 mL) and combined extracts were washed with water (3×100 mL), and dried over anhydrous magnesium sulfate. The solvent was evaporated and the residue was purified by flash chromatography, eluting with hexane/ethyl acetate (1:1) to yield [3S-[ 3α,4β(E)]]-3-(4-fluorophenyl)-N-(6-cyano-3,4-dihydro-3-hydroxy-2,2 -dimethyl-2H-1-benzopyran-4-yl)-3-phenyl-2-propenamide (0.9 g) as a colorless solid, m.p. 128°–130° C. (foaming @120°): $^1$H NMR (CDCl$_3$) δ7.78 (s, 1H), 7.71 (d, J=3.7 Hz, 1H), 7.52 (m, 4H), 7.15 (t, J=8.3 & 17.1 Hz, 1H), 6.95(d, J=8.8 Hz, 1H), 6.55 (d, J=15.8 Hz, 1H), 6.45 (d, J=7.6 Hz, 1H), 5.26 (t, J=8.8 & 17.0 Hz, 1H), 4.62 (d, J=3.5, 1H), 3.83 (dd, J=3.5 Hz, 1H), 1.78 (s, 1H), 1.62, 1.39 (s, 3H each); $^{13}$C NMR (CDCl$_3$) 169.2, 155.3, 142.5, 133.8, 132.7, 130.5, 130.3, 122.0, 119.3, 119.1, 116.7, 116.4, 104.4, 80.9, 76.6, 51.3, 26.8, 18.9;IR(KBr) 831.3, 1126.3, 1231.4, 1491.6, 1510.6, 1615.5, 1661.4, 2226.2, 3420.2 cm$^{-1}$; [α]$_D$$^{25}$=−45.5° (c=0.642, MeOH).

Analysis calculated for C$_{21}$H$_{19}$FN$_2$O$_3$.0.19H$_2$O: C, 68.20; H, 5.28; N, 7.57; F, 5.14; Found: C, 68.25; H, 5.28; N, 7.57; F, 5.14.

EXAMPLE 6

N-(6-Cyano-3,4-dihydro-3-hydroxy-2,3-dimethyl-
2H-1-benzopyran-4-yl)[
1,1'-biphenyl]-2-carboxamide The title compound was prepared from (3S-trans)-4-amino-3,4 -dihydro-3-hydroxy-2,2-dimethyl-2H-1-benzopyran-6-carbonitrile (the title B compound of Example 1) and [1,1'-Biphenyl]-2-carboxylic acid chloride by the same method as described in Example 1, part C. The product was purified by column chromatography on silica gel using 30% ethyl acetate in hexanes to give a white solid m.p. 241°–242° C. [α]$_D$=−48.4° (c=0.73, MeOH).

Analysis calculated for C$_{25}$H$_{22}$N$_2$O$_3$.0.46H$_2$O: C, 73.82; H, 5.68; N, 6.89; Found: C, 73.99; H, 5.45; N, 6.72.

EXAMPLE 7

(3S-trans)-N-(6-Cyano-3,4-dihydro-3-hydroxy-2,
2-dimethyl-2H-1
-benzopyran-4-yl)-2-(9H-fluoren-9-ylidene)acetamide The title compound was prepared from (3S-trans)-4-amino-3,4 -dihydro-3-hydroxy-2,2-dimethyl-2H-1-benzopyran-6-carbonitrile (the title B compound of Example 1) and 2-(9H-fluoren-9-ylidene)acetic acid by the same method as described for the title compound of Example 2. The product was obtained as a light yellow solid, m.p. >300° C.

Analysis calculated for C$_{27}$H$_{22}$N$_2$O$_3$.0.19H$_2$O: C, 76.13; H, 5.30; N, 6.58; Found: C, 76.05; H, 5.28; N, 6.66.

EXAMPLE 8

(3S-trans)-N-(6-Cyano-3,4-dihydro-3-hydroxy-2,2-dimethyl-2H-1-benzopyran-4-yl)-2-(1H-pyrrol-1-yl)benzamide The title compound was prepared from (3S-trans)-4-amino-3,4-dihydro-3-hydroxy-2,2-dimethyl-2H-1-benzopyran-6-carbonitrile (the title B compound of Example 1) and 1-(2-carboxyphenol)-pyrrole (500 mgs, 2.67 mmol) by the same method as described for the title compound of Example 2 to give a white powder, m.p. 226°–228° C. $[\alpha]_D = -16.5°$ (c=0.60, MeOH).

Analysis calculated for $C_{23}H_{21}N_3O_3 \cdot 0.39\ H_2O$: C 70.02; H 5.57; N 10.65; Found: C 69.69; H 5.43; N 10.56.

EXAMPLE 9

(3S-trans)-N-(6-Cyano-3,4-dihydro-3-hydroxy-2,2-dimethyl-2H-1-benzopyran-4-yl)-2-phenyl-1-cyclopentenamide

A. 1-(trifluoracetoxy)cyclopentene-2-carboxylic acid methyl ester

A solution of diisopropylamine (2.17 mL, 15.5 mmol) in tetrahydrofuran (50 mL), under argon was cooled to −10° C. and treated slowly with a 2.5M solution of n-butyllithium in hexanes (5.9 mL, 16.3 mmol). The resultant solution was stirred for 30 minutes and then cooled to −78° C. A solution of the cyclopentanone-2-carboxylic acid methyl ester (1.75 mL, 14.1 mmol) in tetrahydrofuran (10 mL) was added and the reaction mixture was stirred for one hour at −78° C. It was allowed to warm to 0° C. and N-phenyltrifluoromethanesulfonimide (5.5 g, 15.5 mmol) was added. The reaction mixture was stirred at room temperature for 18 hours and diluted with ether (100 mL). The solution was washed with 5% potassium hydrogensulfate (100 mL), water (100 mL), brine (100 mL) and dried over magnesium sulfate. The solvent was removed and the residue was purified by flash chromatography on silica gel (5% ethyl acetate in hexanes) to give a yellowish oil (1.0 g, 58%).

B. 2-Phenyl-1-cyclopentenecarboxylic acid methyl ester

A solution of the title A compound (1.66 g, 6.43 mmol) in dioxane (50 mL) was treated with lithium chloride (818 mgs, 6.75 mmol), phenyltrimethyltin (1.05 mL, 6.75 mmol) and tetrakis(triphenylphosphine)palladium catalyst (149 mgs, 0.13 mmol). The reation mixture was heated at reflux for two hours. The solution was cooled, treated with pyridine (1.14 mL, 14.1 mmol) followed by hydrogen fluoride/pyridine complex (865 μL, 7.07 mmol) and stirred for 18 hours at room temperature. The resultant solution was diluted with ether (100 mL) and filtered through a short plug of celite. The organic solution was washed with 1N hydrochloric acid, water, and brine. After drying (magnesium sulfate), the solvent was removed and the residue was purified by flash chromatography (5% ethyl acetate in hexane) to give a colorless oil (1.0 g, 58%).

C. 2-Phenyl-1-cyclopentenecarboxylic acid

A solution of title B compound (1.20 g, 5.9 mmol) in dimethylsulfoxide (20 mL)/water (20 mL) was treated with a 1N potassium hydroxide solution (8.9 mL, 8.9 mmol) and the reaction mixture was stirred at 50° C. for 18 hours. The reaction mixture was acidified with potassium hydrogensulfate and extracted with ether. The organic extracts were dried (magnesium sulfate) and the solution was treated with hexane to precipitate out the product which was used without further purification.

D. (3S-trans)-N-(6-Cyano-3,4-dihydro-3-hydroxy-2,2-dimethyl-2H-1-benzopyran-4-yl]-2-phenyl-1-cyclopentenamide The title compound was prepared from (3S-trans)-4-amino-3,4-dihydro-3-hydroxy-2,2-dimethyl-2H-1-benzopyran-6-carbonitrile (the title B compound of Example 1) and 2-phenyl-1-cyclopentenecarboxylic acid (the title C compound) by the same method as described for the compound of Example 2 to give a white powder, m.p. 156°–158° C. $[\alpha]_D = +36.8°$ (c=0.72, MeOH).

Analysis calculated for $C_{24}H_{24}N_2O_3 \cdot 0.23H_2O$: C, 73.43; H, 6.28; N, 7.14; Found: C, 73.42; H, 6.14; N, 7.15.

EXAMPLE 10

(3S-trans)-N-(6-Cyano-3,4-dihydro-3-hydroxy-2,2-dimethyl-2H-1-benzopyran-4-yl)-4-phenyl-1,2,3-thiadiazole-5-carboxamide The title compound was prepared from (3S-trans)-4-amino-3,4-dihydro-3-hydroxy-2,2-dimethyl-2H-1-benzopyran-6-carbonitrile (the title B compound of Example 1) and 4-phenyl-1,2,3-thiadiazole-5-carboxylic acid by the same method as described for the title compound of Example 2 to give a colorless solid, m.p. 185° C. (decomposed). $[\alpha]_D = -26.2°$ (c=0.80, MeOH).

Analysis calculated for $C_{21}H_{18}N_4O_3S \cdot 0.80$ 2-propanol: C, 61.74; H, 5.42; N, 12.31; S, 7.04; Found: C, 61.74; H, 5.50; N, 12.14; S, 7.00.

EXAMPLE 11

[(3S-[3α,4β(E)]]-N-(6-Cyano-3,4-dihydro-3-hydroxy-2,2-dimethyl-2H-1-benzopyran-4-yl)-3-(6-nitro-1,3-benzodioxol-5-yl)-2-propenamide The title compound was prepared from (3S-trans)-4-amino-3,4-dihydro-3-hydroxy-2,2-dimethyl-2H-1-benzopyran-6-carbonitrile (the title B compound of Example 1) and (E)-(3-(4,5-methylenedioxy-2nitrophenyl)propenoic acid by the same method as described for the title compound of Example 2 to afford a yellow solid, m.p. 202°–210° C. $[\alpha]_D = -36.2°$ (c=0.58, MeOH).

Analysis calculated for $C_{22}H_{19}N_3O_7 \cdot 0.50$ hexane $\cdot 0.23\ H_2O$: C, 61.94; H, 5.42; N, 8.67; Found: C, 61.93; H, 5.43; N, 8.71.

EXAMPLE 12

(3 S-trans)-N-(6-Cyano-3,4-dihydro-3-hydroxy-2,2-dimethyl-2H-1-benzopyran-4-yl)-1-(3-ethynylphenyl)-5-phenyl-1,2,3-triazole-5-carboxamide The title compound was prepared from (3S-trans)-4-amino-3,4-dihydro-3-hydroxy-2,2-dimethyl-2H-1-benzopyran-6-carbonitrile (the title B compound of Example 1) and 1-(3-ethynylphenyl)-5-phenyl-1,2,3-triazole-5-carboxylic acid by the same method as described for the title compound of Example 2 to afford a white solid, m.p.

115°–125° C. (softens at 81° C.). $[\alpha]_D=-110.1°$ (c=0.69, MeOH).

Analysis calculated for $C_{29}H_{23}N_5O_3 \cdot 0.4\ CHCl_3 \cdot 0.40\ H_2O$: C, 63.99; H, 4.57; N, 12.69; Found: C, 63.99; H, 4.20; N, 12.62.

EXAMPLE 13

(3S-trans)-N-(6-Cyano-3,4-dihydro-3-hydroxy-2,2-dimethyl-2H-1-benzopyran-4-yl)-5-methyl-3-phenyl-4-isoxazolecarboxamide The title compound was prepared from (3S-trans)-4-amino-3,4-dihydro-3-hydroxy-2,2-dimethyl-2H-1-benzopyran-6-carbonitrile (the title B compound of Example 1) and 5-methyl-3-phenylisoxazole-4-carboxlic acid by the same method as described for the title compound of Example 2 to afford a white solid, m.p. 235°–236° C. $[\alpha]_D=-29.6°$ (c=0.46, MeOH).

Analysis calculated for $C_{23}H_{21}N_3O_4$: C, 68.47; H, 5.25; N, 10.42; Found: C, 68.35; H, 5.24; N, 10.40.

EXAMPLE 14

(3S-trans)-N-(6-Cyano-3,4-dihydro-3-hydroxy-2,2-dimethyl-2H-1-benzopyran-4-yl)-5-phenyl-4-oxazolecarboxamide The title compound was prepared from (3S-trans)-4-amino-3,4-dihydro-3-hydroxy-2,2-dimethyl-2H-1-benzopyran-6-carbonitrile (the title B compound of Example 1) and 5-phenyl-4-oxazolecarboxylic acid by the same method as described for the title compound of Example 2 to afford an off-white solid, m.p. 196°–197° C. $[\alpha]_D=-179.8°$ (c=0.40, MeOH).

Analysis calculated for $C_{22}H_{19}N_3O_4 \cdot 0.16\ H_2O$: C, 67.35; H, 4.96; N, 10.71; Found: C, 67.33; H, 4.91; N, 10.73.

EXAMPLE 15

(3S-trans)-N-(6-Cyano-3,4-dihydro-3-hydroxy-2,2-dimethyl-2H-1-benzopyran-4-yl)-4-(1H-pyrrol-1-yl)-3-thiophenecarboxamide The title compound was prepared from (3S-trans)-4-amino-3,4-dihydro-3-hydroxy-2,2-dimethyl-2H-1-benzopyran-6-carbonitrile (the title B compound of Example 1) and 4-(1H-pyyrol-1-yl)-3-thiophene carboxylic acid by the same method as described in Example 2 to afford a white solid, m.p. 174°–175° C. $[\alpha]_D=-42.4°$ (c=0.45, MeOH).

Analysis calculated for $C_{21}H_{19}N_3O_3S$: C, 64.11; H, 4.87; N, 10.68; S, 8.15; Found: C, 64.10; H, 4.88; N, 10.47; S, 8.17.

What is claimed is:
1. A compound of the formula

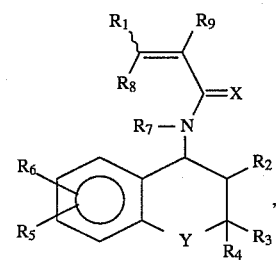

or pharmaceutically acceptable salts thereof, wherein

X is oxygen or sulfur;

$R_1$ is aryl;

$R_2$ is hydrogen, hydroxy or

$R_3$ and $R_4$ are each independently hydrogen, alkyl or arylalkyl; or, $R_3$ and $R_4$ when bonded to the same carbon atom, taken together with the carbon atom to which they are attached form a 5- to 7-membered carbocyclic ring;

$R_5$ is hydrogen, alkyl, haloalkyl, alkenyl, alkynyl, cycloalkyl, arylalkyl, cycloalkylalkyl, —CN, —NO$_2$, —COR, —COOR, —CONHR, —CON(R)$_2$, —CF$_3$, —S-alkyl, —SOalkyl, —SO$_2$alkyl,

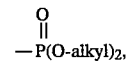

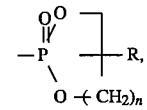

halogen, amino, substituted amino, —O-alkyl, —OCF$_3$, —OCH$_2$CF$_3$, —OCOalkyl, —OCONRalkyl, —NRCOalkyl, —NRCOOalkyl or —NRCON(R)$_2$ wherein R is hydrogen, alkyl, aryl, arylalkyl, cycloalkyl, or (cycloalkyl)alkyl or haloalkyl;

$R_6$ is hydrogen, alkyl, halo, —OH, —O-alkyl, amino, substituted amino, —O-alkyl, —OCOalkyl, —OCONRalkyl, —NRCOalkyl, —NRCOOalkyl or —NRCON(R)$_2$;

$R_7$ is hydrogen, alkyl or arylalkyl;

$R_8$ is hydrogen, alkyl, aryl or —O-alkyl;

$R_9$ is hydrogen, alkyl, aryl, —COO-alkyl or —CO-alkyl; or

Y is —O—; and n is an integer of 1, 2 or 3.

2. A compound of claim 1 wherein $R_1$ is aryl;

$R_2$ is hydrogen or hydroxy;

$R_3$ and $R_4$ are each alkyl;

$R_5$ is —CN, —NO$_2$, —COR, —COOR, —CONHR, —CON(R)$_2$, —CF$_3$, —SOalkyl, —SO$_2$alkyl,

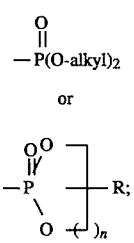

$R_6$ is hydrogen, alkyl or O-alkyl;
$R_7$ is hydrogen;
$R_8$ is hydrogen; and
$R_9$ is hydrogen.

3. A compound of claim 1 wherein
$R_1$ is phenyl, 4-chlorophenyl or 4-fluorophenyl;
$R_2$ is trans-hydroxy;
$R_3$ and $R_4$ are each methyl;
$R_5$ is —CN or —NO$_2$;
$R_6$ is hydrogen;
$R_7$ is hydrogen;
$R_8$ is hydrogen; and
$R_9$ is hydrogen;
where $R_1$ and $R_9$ are in a trans arrangement.

4. A compound of claim 1 having the name [3S-[3α, 4β(E)]]-N-(6-cyano-3,4-dihydro-3-hydroxy-2,2-dimethyl-2H-1-benzopyran-4-yl)-3-phenyl-2-propenamide.

5. A compound of claim 1 having the name [3S-[3α, 4β(E)]]-3-(4-chlorophenyl)-N-(6-cyano-3,4-dihydro-3-hydroxy-2,2-dimethyl-2H-1-benzopyran-4-yl)-3-phenyl-2-propenamide.

6. A compound of claim 1 having the name [3S-[3α, 4β(E)]]-3-(3-chlorophenyl)-N-(6-cyano-3,4-dihydro-3-hydroxy-2,2-dimethyl-2H-1-benzopyran-4-yl)-2-propenamide.

7. A compund of claim 1 having the name [3S-[3α,4β(Z)]]-N-(6-cyano-3,4-dihydro-3-hydroxy-2,2-dimethyl-2H-1-benzopyran-4-yl)-3-phenyl-2-propenamide.

8. A compound of claim 1 having the name [3S-[3α, 4β(E)]]-3-(4-fluorophenyl)-N-(6-cyano-3,4-dihydro-3-hydroxy-2,2-dimethyl-2H-1-benzopyran-4-yl)-2-propenamide.

9. A pharmaceutical composition comprising a compound of claim 1 and a pharmaceutically acceptable carrier therefor.

10. A method for the treatment of ischemic conditions in a mammalian specie comprising providing to a specie in need thereof an effective amount of a composition of claim 9.

* * * * *